United States Patent [19]

Lechaude et al.

[11] Patent Number: 5,346,594
[45] Date of Patent: Sep. 13, 1994

[54] PROCESS FOR THE PURIFICATION OF 1,1-DICHLORO-1-FLUOROETHANE

[75] Inventors: Paul Lechaude, Brussels, Belgium; Gilles Darago; Philippe Krafft, both of Tavaux, France; Jean-Pierre Catinat, Binche, Belgium

[73] Assignee: Solvay (Société Anonyme), Brussels, Belgium

[21] Appl. No.: 2,765

[22] Filed: Jan. 12, 1993

[30] Foreign Application Priority Data

Jan. 13, 1992 [BE] Belgium ............... 09200026

[51] Int. Cl.$^5$ ............... B01D 3/34; C07C 17/38
[52] U.S. Cl. ............... 203/29; 203/34; 570/178
[58] Field of Search ............... 203/29, 34, 91, DIG. 6; 570/177, 178

[56] References Cited

U.S. PATENT DOCUMENTS

| | | | |
|---|---|---|---|
| 4,028,426 | 6/1977 | Mansell | 570/238 |
| 4,950,816 | 8/1990 | Tung et al. | 570/179 |
| 4,962,244 | 10/1990 | Elsheikh | 570/165 |
| 5,051,538 | 9/1991 | Gumprecht | 570/166 |

FOREIGN PATENT DOCUMENTS

| | | |
|---|---|---|
| 626454 | 3/1991 | Australia . |
| 0420709 | 4/1991 | European Pat. Off. . |
| 1036233 | 2/1986 | Japan . |
| 4099737 | 3/1992 | Japan . |

OTHER PUBLICATIONS

CA 88(18): 128 951V.
CA 114(1): 5801 U.
CA 116(7): 58736Z.

*Primary Examiner*—Virginia Manoharan
*Attorney, Agent, or Firm*—Spencer, Frank & Schneider

[57] ABSTRACT

A process for purification of crude, 1,1-dichloro-1-fluoroethane includes the steps of treating a mixture of crude, 1,1-dichloro-1-fluoroethane and hydrogen fluoride with chlorine in the presence of a Lewis acid, and distilling to recover purified 1,1-dichloro-1-fluoroethane, wherein hydrogen fluoride is present during the treatment with chlorine at a ratio of at least 5% by weight with respect to the mixture of crude, 1,1-dichloro-1-fluoroethane and hydrogen fluoride.

8 Claims, No Drawings

PROCESS FOR THE PURIFICATION OF 1,1-DICHLORO-1-FLUOROETHANE

BACKGROUND OF THE INVENTION

Field of the Invention

The present invention relates to an improved process for the purification of 1,1-dichloro-1-fluoroethane by treatment with chlorine followed by distillation.

Description of the Related Art 1,1-Dichloro-1-fluoroethane (HFA-141b) is a partially halogenated chlorofluorinated hydrocarbon which is proving to be an advantageous substitute for some entirely halogenated chlorofluorocarbons (CFCs) whose production and use are progressively reduced because they are suspected of having a harmful effect on the ozone layer.

The compositions resulting from the processes for the preparation of 1,1-dichloro-1-fluoroethane contain byproducts and undesirable impurities. Some of these byproducts and impurities can be easily separated by distillation. This is especially the case for 1-chloro-1,1-difluoroethane and 1,1,1-trifluoroethane, as well as for the oligomers formed during reaction. However, 1,1-dichloro-1-fluoroethane generally contains, as impurities, small quantities of chlorinated and/or chlorofluorinated unsaturated compounds whose separation by distillation proves to be difficult, given their boiling point in the region of that of 1,1-dichloro-1-fluoroethane.

Besides vinylidene chloride, which is the most significant impurity, the unsaturated impurities which can be present in 1,1-dichloro-1-fluoroethane to be purified are mainly cis and trans 1,2-dichloro-1-fluoroethylenes, trans 1,2-dichloroethylene, as well as traces of dichloroacetylene and 1-chloro-1-fluoroethylene.

The Patent Application EP-A-0,420,709 by Atochem describes the purification of 1,1-dichloro-1-fluoroethane essentially from vinylidene chloride and dichloroacetylene by reacting with chlorine and/or a hydracid, with a molar ratio between, on the one hand, chlorine and/or the hydracid and, on the other hand, vinylidene chloride which is at least equal to 1.2 and which can range up to 10, in the presence of 0.001 to 1% by weight of Lewis acid with respect to the crude product to be treated, followed by a separation by distillation. The majority of the examples describe the chlorination of the impurities using chlorine in the absence of hydracid. Example 9 describes the chlorination in the presence of SbCl$_5$ of a sample drawn off from a manufacture of 1,1-dichloro-1-fluoroethane and 1-chloro-1,1-difluoroethane containing 2% by weight of hydracid (HCl plus HF) for 3 hours at 9° C. to obtain a purified product containing less than 70 ppm of vinylidene chloride.

This process of the prior art consequently does not make possible a rapid purification from vinylidene chloride in the presence of a Lewis acid and hydrogen fluoride. Moreover, the removal of cis and trans 1,2-dichloro-1-fluoroethylenes appears difficult because it was observed that, in certain cases, after most of the cis and trans 1,2-dichloro-1-fluoroethylenes are removed, its concentration grows if the chlorination treatment is prolonged. Finally, the use of Lewis acid in quantities such as recommended in this application can result in a significant degradation of 1,1-dichloro-1-fluoroethane downstream of the chlorination stage.

The aim of the present invention is consequently to provide an improved process for the purification of crude 1,1-dichloro-1-fluoroethane by treatment of the unsaturated impurities, both chlorinated and chlorofluorinated, with chlorine in order to form saturated compounds which are easily separated by distillation which is rapid and causes no significant degradation of 1,1-dichloro-1-fluoroethane.

SUMMARY OF THE INVENTION

To that end, the invention relates to a process for the purification of crude 1,1dichloro-1-fluoroethane by treatment with chlorine in the presence of Lewis acid and hydrogen fluoride and then distillation, hydrogen fluoride being present during the treatment with chlorine at a ratio of at least 5% by weight with respect to the mixture of crude 1,1-dichloro-1-fluoroethane and hydrogen fluoride.

DESCRIPTION OF THE PREFERRED EMBODIMENTS

A surprising effect of the present invention lies in the fact that the implementation of the treatment stage with chlorine in the presence of small amounts of hydrogen fluoride provides results which are less good than in the absence of hydrogen fluoride, whereas, in the presence of at least 5% by weight of hydrogen fluoride with respect to the mixture of crude 1,1-dichloro-1fluoroethane and hydrogen fluoride, chlorination of the unsaturated impurities is markedly faster.

Most often, the treatment with chlorine is carried out in the presence of at least 15% by weight of hydrogen fluoride. The maximum amount of hydrogen fluoride used during the treatment with chlorine is not absolutely critical. Nevertheless, for the purpose of restricting degradation of 1,1-dichloro-1-fluoroethane to 1-chloro-1,1-difluoroethane and the excess of hydrogen fluoride to be recycled downstream of the purification treatment, it is preferable not to exceed 50% by weight of hydrogen fluoride with respect to the mixture of crude 1,1-dichloro-1-fluoroethane and hydrogen fluoride.

In practice, the required hydrogen fluoride can arise in total or in part from the initial excess of hydrogen fluoride used for the preparation of 1,1-dichloro-1-fluoroethane and from then on present in the crude 1,1-dichloro-1-fluoroethane to be treated. The treatment stage with chlorine can then be carried out without prior separation of the unreacted hydrogen fluoride and optionally without addition of hydrogen fluoride for the single chlorination stage of the unsaturated impurities contained in crude 1,1-dichloro-1-fluoroethane.

Moreover, the amount of Lewis acid used is advantageously less than 10 ppm with respect to crude 1,1-dichloro-1-fluoroethane to be treated to prevent an excessive degradation of 1,1-dichloro-1-fluoroethane downstream of the present stage, especially in the following distillation stages. The amount of Lewis acid used can be as low as 0.15 ppm. Although this amount is very low, the presence of a Lewis acid remains indispensable to achieve chlorination of all the unsaturated impurities. Preferably, at least 1.5 ppm of Lewis acid is used.

Another surprising aspect of the invention lies in the fact that the use of such low quantities of Lewis acid proves to be very efficient for the purpose of purifying 1,1-dichloro-1-fluoroethane from unsaturated impurities. Given the very small amounts of Lewis acid used, the process according to the invention additionally has the advantage of rendering superfluous a stage for the removal of the Lewis acid, by washing with an acidic aqueous solution or by complexing, prior to any subsequent stage, whereas such a stage is necessary in order to prevent degradation of 1,1-dichloro-1-fluoroethane and reappearance of unsaturated impurities when the treatment with chlorine is carried out in the presence of more significant quantities of Lewis acid.

Generally, the Lewis acid is chosen from $FeCl_3$, $SnCl_4$, $SbCl_5$, $MoCl_5$, $TiCl_4$ and their mixtures. Preferably, $FeCl_3$ is used.

The Lewis acid can be introduced in various forms and in various ways. It can especially be introduced by dissolving in a fraction of crude 1,1-dichloro-1-fluoroethane flow or in the form of a solution in other solvents, such as especially tetrachloromethane, trichloromethane or 1,2-dichloroethane.

The very small amount of Lewis acid required according to the invention can be formed, in all or in part, from the metal arising from the plant, optionally without requiring external supply. In particular, $FeCl_3$ can be generated in situ from iron arising from the plant. It can especially be thus when the plant comprises at least one recycling loop, for example of hydrogen fluoride. In this case, it is advisable to monitor the amount of iron which is circulating in the plant in order to prevent it exceeding the amount allowed according to the invention and resulting in the disadvantages already mentioned.

Chlorine is introduced in excess amounts with respect to the unsaturated impurities to be chlorinated. Generally, the treatment with chlorine is carried out in the presence of at least 0.1% by weight of chlorine with respect to the weight of crude 1,1-dichloro-1-fluoroethane to be treated. Most often, the proportion of chlorine does not exceed 12%. Preferably, at least 1.5% by weight of chlorine is used. Advantageously, the proportion of chlorine used is preferably not more than 8% by weight with respect to the weight of crude 1,1-dichloro-1-fluoroethane to be treated.

The treatment with chlorine can be carried out at a temperature generally of at least 0° C. To obtain a good chlorination rate, it is preferable to work at a temperature of at least 60° C. To prevent significant degradation of 1,1-dichloro-1-fluoroethane to 1,1,2-trichloro-1-fluoroethane and the reformation of cis and trans 1,2-dichloro-1-fluoroethylenes, it is particularly preferable not to exceed a temperature of 90° C.

The treatment with chlorine can be carried out at atmospheric pressure or at a pressure greater than atmospheric pressure. This pressure can be autogenous pressure or a greater pressure generated by the introduction of an inert gas such as helium.

Under the accepted operating conditions according to the invention, a virtually complete chlorination of the chlorinated and chlorofluorinated unsaturated impurities can be carried out with a treatment time of 1 to 60 minutes. Preferably, the treatment with chlorine lasts at least 2 minutes. To restrict degradation of 1,1-dichloro-1-fluoroethane and the reformation of cis and trans 1,2-dichloro-1-fluoroethylenes, it is preferred not to exceed 30 minutes. Excellent results are observed with a treatment time of approximately 15 minutes.

In order especially to avoid generating excessive amounts of $FeCl_3$ in the medium, the chlorination reactor and the equipment downstream are preferably made of materials which are resistant to corrosion, such as especially the alloys Monel, Inconel and Hastelloy.

After the treatment with chlorine, high-purity 1,1-dichloro-1-fluoroethane is obtained by removing, by distillation, the inorganics, essentially hydrogen fluoride and unreacted chlorine, which can optionally be recycled, and then the compounds which are lighter and heavier than 1,1-dichloro-1-fluoroethane and which were initially present or formed during the treatment with chlorine.

Example 1 is given with the aim of illustrating the invention but it is in no way limiting. Examples 2 and 3 are given by way of reference.

EXAMPLES

Example 1

253 g of 1,1-dichloro-1-fluoroethane to be purified, containing 3.8 ppm of $FeCl_3$, are sucked into a 0.5 liter autoclave made of Hastelloy alloy, equipped with a stirrer, cooled beforehand to $-35°$ C. and put under a vacuum of 1,500 Pa. 120 g of hydrogen fluoride, maintained beforehand at room temperature in a cylinder made of stainless steel, are added thereto. The mixture of crude 1,1-dichloro-1-fluoroethane and hydrogen fluoride thus comprises 32% by weight of hydrogen fluoride.

The reaction mixture is then brought to 55° C. by immersing the reactor in a preheated, thermostatically-controlled bath. The pressure at this stage is $5.10^5$ Pa. 9.6 g of chlorine from a cylinder are then introduced. The temperature moves to 65° C. and is maintained at this value whereas the autogenous pressure increases during the trial to reach approximately $7.5.10^5$ Pa after 15 minutes.

Samples are withdrawn using a dip pipe. They are collected directly in a separating funnel containing a two-phase mixture consisting of a saturated aqueous sodium bicarbonate solution and carbon tetrachloride. After separating and drying over $CaCl_2$, the organic phase is analysed by gas phase chromatography.

Table 1 takes in the contents (relative to 1,1-dichloro-1-fluoroethane) of chlorinated and chlorofluorinated impurities in the initial mixture of 1,1dichloro-1-fluoroethane and hydrogen fluoride and then 15 minutes after the introduction of chlorine.

TABLE 1

| | Concentration (mg/kg HFA-141b) | |
|---|---|---|
| | Initial reaction mixture | After treatment t = 15 min. |
| Vinylidene chloride | 2250 | <3 |
| Dichloroacetylene | 2 | <3 |
| trans 1,2-Dichloro-ethylene | 187 | <3 |
| cis 1,2-Dichloro-1-fluoroethylene | 105 | <3 |
| trans 1,2-Dichloro-1-fluoroethylene | 104 | <3 |
| 1-Chloro-1-fluoro-ethylene | 6 | <3 |
| 1-Chloro-1,1-difluoroethane | 12 | 2060 |

After treating for only 15 minutes, there only remains in the mixture less and 3 ppm of each of the unsaturated impurities examined, especially of vinylidene chloride. The formation of 1-chloro-1,1-difluoroethane, easily separable from 1,1-dichloro-1-fluoroethane by distillation, is also observed.

High-purity 1,1-dichloro-1-fluoroethane can then easily be obtained by distillation.

Example 2 R 380 g of 1,1-dichloro-1-fluoroethane to be purified containing 3.2 ppm of $FeCl_3$ are sucked into a 0.5 liter autoclave made of Hastelloy alloy, equipped with a stirrer, cooled beforehand to $-35°$ C. and put under a vacuum of 1500 Pa. Hydrogen fluoride is not added thereto.

The reaction mixture is then brought to 58° C. by immersing the reactor in a preheated, thermostatically-controlled bath. The pressure at this stage is $2.2.10^5$ Pa. 16 g of chlorine from a cylinder are then introduced. The temperature moves to 65° C. and is maintained at this value whereas the autogenous pressure increases during the trial to reach approximately $3.8.10^5$ Pa after 15 minutes.

Samples are withdrawn using a dip pipe. They are collected directly in a separating funnel containing a saturated aqueous sodium bicarbonate solution. After separating and drying over $CaCl_2$, the organic phase is analysed by gas phase chromatography.

Table 2 takes in the contents (relative to 1,1-dichloro-1-fluoroethane) of chlorinated and chlorofluorinated impurities in the initial mixture of 1,1-dichloro-1-fluoroethane and then 15 minutes after the introduction of chlorine.

TABLE 2

| | Concentration (mg/kg HFA-141b) | |
|---|---|---|
| | Initial reaction mixture | After treatment t = 15 min. |
| Vinylidene chloride | 2200 | 660 |
| Dichloroacetylene | 3 | 1 |
| trans 1,2-Dichloroethylene | 190 | 77 |
| cis 1,2-Dichloro-1-fluoroethylene | 106 | 51 |
| trans 1,2-Dichloro-1-fluoroethylene | 112 | 64 |
| 1-Chloro-1-fluoroethylene | 5 | 2 |
| 1-Chloro-1,1-difluoroethane | 13 | 7 |

Example 3 R 381 g of 1,1-dichloro-1-fluoroethane to be purified containing 4.6 ppm of $FeCl_3$ are sucked into a 0.5 liter autoclave made of Hastelloy alloy, equipped with a stirrer, cooled beforehand to $-35°$ C. and put under a vacuum of 1500 Pa. 2 g of hydrogen fluoride, maintained beforehand at room temperature in a cylinder made of stainless steel, are added thereto. The mixture of crude 1,1-dichloro-1-fluoroethane and hydrogen fluoride thus comprises 0.5% by weight of hydrogen fluoride.

The reaction mixture is then brought to 60° C. by immersing the reactor in a preheated, therostatically-controlled bath. The pressure at this stage is $3.2.10^5$ Pa. 22.9 g of chlorine from a cylinder are then introduced. The temperature moves to 65° C. and is maintained at this value whereas the autogenous pressure increases during the trial to reach approximately $4.5.10^5$ Pa after 15 minutes.

Samples are withdrawn using a dip pipe. They are collected directly in a separating funnel containing a two-phase mixture consisting of a saturated aqueous sodium bicarbonate solution and carbon tetrachloride. After separating and drying over $CaCl_2$, the organic phase is analysed by gas phase chromatography.

Table 3 takes in the contents (relative to 1,1-dichloro-1-fluoroethane) of chlorinated and chlorofluorinated impurities in the initial mixture of 1,1-dichloro-1-fluoroethane and hydrogen fluoride and then 15 minutes after the introduction of chlorine.

TABLE 3

| | Concentration (mg/kg HFA-141b) | |
|---|---|---|
| | Initial reaction mixture | After treatment t = 15 min. |
| Vinylidene chloride | 1965 | 935 |
| Dichloroacetylene | 14 | <3 |
| trans 1,2-Dichloroethylene | 158 | 109 |
| cis 1,2-Dichloro-1-fluoroethylene | 101 | 94 |
| trans 1,2-Dichloro-1-fluoroethylene | 122 | 94 |
| 1-Chloro-1-fluoroethylene | 7 | 3 |
| 1-Chloro-1,1-difluoroethane | 14 | 12 |

Comparison of the results of Example 1, according to the invention, with those of Example 2 and 3, given by way of reference, bears witness, on the one hand, to the remarkable efficiency of the process according to the invention and, on the other hand, to the suprising results to which it leads, to the extent that the absence of hydrogen fluoride (Reference Example 2) leads to better results than those obtained in the presence of an amount of hydrogen fluoride less than (Reference Example 3) that used in the process according to the invention.

What is claimed is:

1. Process for purification of crude 1,1-dichloro-1-fluoroethane, comprising:
   (a) treating a mixture consisting essentially of crude 1,1-dichloro-1-fluoroethane and hydrogen fluoride with chlorine at a ratio of chlorine which does not exceed 50% by weight based on the weight of the mixture of crude 1,1-dichloro-1-fluoroethane and hydrogen fluoride in the presence of a Lewis acid; and
   (b) distilling to recover purified 1,1-dichloro-1-fluoroethane, wherein hydrogen fluoride is present during the treatment with chlorine at a ratio of at least 5% by weight with respect to the mixture of crude 1,1-dichloro-1-fluoroethane and hydrogen fluoride.

2. Process according to claim 1, wherein hydrogen fluoride is present during the treatment with chlorine at a ratio of at least 15% by weight with respect to the mixture of crude 1,1-dichloro-1-fluoroethane and hydrogen fluoride.

3. Process according to claim 1, wherein the treatment with chlorine is carried out in the presence of less than 10 ppm of a Lewis acid with respect to the weight of crude 1,1-dichloro-1fluoroethane.

4. Process according to claim 1, wherein the treatment with chlorine is carried out in the presence of at least 0.15 ppm of a Lewis acid with respect to the weight of crude 1,1-dichloro-1-fluoroethane.

5. Process according to claim 1, wherein the Lewis acid is $FeCl_3$.

6. Process according to claim 1, wherein the treatment with chlorine is carried out in the presence of from 0.1 to 12% by weight of chlorine with respect to the weight of crude 1,1-dichloro-1-fluoroethane.

7. Process according to claim 1, wherein the treatment with chlorine is carried out at a temperature ranging from 0° and 90° C.

8. Process according to claim 1, wherein the treatment with chlorine does not exceed 30 minutes.

* * * * *